US011573182B2

(12) United States Patent
Roederer et al.

(10) Patent No.: US 11,573,182 B2
(45) Date of Patent: Feb. 7, 2023

(54) VISUALIZATION, COMPARATIVE ANALYSIS, AND AUTOMATED DIFFERENCE DETECTION FOR LARGE MULTI-PARAMETER DATA SETS

(71) Applicant: FlowJo, LLC, Ashland, OR (US)

(72) Inventors: Mario Roederer, Bethesda, MD (US); Michael D. Stadnisky, Ashland, OR (US)

(73) Assignee: FlowJo, LLC, Ashland, OR (US)

(*) Notice: Subject to any disclaimer, the term of this patent is extended or adjusted under 35 U.S.C. 154(b) by 1293 days.

(21) Appl. No.: 15/987,713

(22) Filed: May 23, 2018

(65) Prior Publication Data

US 2018/0340890 A1 Nov. 29, 2018

Related U.S. Application Data

(60) Provisional application No. 62/511,342, filed on May 25, 2017.

(51) Int. Cl.

| | |
|---|---|
| G01N 21/64 | (2006.01) |
| G16B 40/00 | (2019.01) |
| G16B 45/00 | (2019.01) |
| G06F 17/18 | (2006.01) |
| G01N 15/14 | (2006.01) |
| G06K 9/62 | (2022.01) |
| G16B 40/30 | (2019.01) |
| G06V 10/75 | (2022.01) |
| G06V 20/69 | (2022.01) |

(52) U.S. Cl.
CPC ......... *G01N 21/6486* (2013.01); *G01N 15/14* (2013.01); *G06F 17/18* (2013.01); *G06K 9/6277* (2013.01); *G06V 10/758* (2022.01); *G06V 20/698* (2022.01); *G16B 40/00* (2019.02); *G16B 40/30* (2019.02); *G16B 45/00* (2019.02); *G01N 2015/1402* (2013.01); *G01N 2015/1477* (2013.01); *G06K 9/6232* (2013.01)

(58) Field of Classification Search
None
See application file for complete search history.

(56) References Cited

U.S. PATENT DOCUMENTS

| | | | |
|---|---|---|---|
| 4,845,653 A | 7/1989 | Conrad et al. | |
| 5,627,040 A | 5/1997 | Bierre et al. | |
| 5,739,000 A | 4/1998 | Bierre et al. | |
| 5,795,727 A | 8/1998 | Bierre et al. | |
| 5,962,238 A | 10/1999 | Sizto et al. | |
| 6,014,904 A | 1/2000 | Lock | |
| 6,221,592 B1 | 4/2001 | Schwartz et al. | |
| 6,560,546 B1 | 5/2003 | Shenk et al. | |
| 6,769,030 B1 | 7/2004 | Bournas | |
| 6,944,338 B2 | 9/2005 | Lock et al. | |
| 7,010,582 B1 | 3/2006 | Cheng et al. | |
| 7,194,531 B2 | 3/2007 | Donker et al. | |
| 7,277,938 B2 | 10/2007 | Duimovich et al. | |
| 7,356,598 B1 | 4/2008 | Giroir | |
| 7,472,342 B2 | 12/2008 | Haut | |
| 7,492,372 B2 * | 2/2009 | Abshear | G16B 45/00 345/581 |
| 8,835,358 B2 | 9/2014 | Fodor et al. | |
| 9,567,645 B2 | 2/2017 | Fan et al. | |
| 9,762,598 B1 | 9/2017 | Jagpal et al. | |
| 2002/0067358 A1 | 6/2002 | Casara et al. | |
| 2003/0009470 A1 | 1/2003 | Leary | |
| 2003/0078703 A1 | 4/2003 | Potts et al. | |
| 2003/0088657 A1 | 5/2003 | Eggers | |
| 2004/0019690 A1 | 1/2004 | Cardno | |
| 2004/0061713 A1 | 4/2004 | Jennings | |
| 2004/0161767 A1 | 8/2004 | Baldwin et al. | |
| 2004/0242216 A1 | 12/2004 | Boutsikakis | |
| 2004/0250118 A1 | 12/2004 | Andreev et al. | |
| 2005/0038608 A1 | 2/2005 | Chandra et al. | |
| 2005/0239125 A1 | 10/2005 | Hodge | |
| 2005/0247114 A1 | 11/2005 | Kahn et al. | |
| 2005/0272085 A1 | 12/2005 | Hodge | |
| 2006/0014192 A1 | 1/2006 | Hodge | |
| 2006/0063264 A1 | 3/2006 | Turner et al. | |
| 2006/0148063 A1 | 7/2006 | Fauzzi | |
| 2007/0014305 A1 | 1/2007 | Assad | |

(Continued)

FOREIGN PATENT DOCUMENTS

| | | |
|---|---|---|
| JP | 62-31815 | 2/1987 |
| JP | 63-259442 | 10/1988 |

(Continued)

OTHER PUBLICATIONS

Archival Cytometry Standard, Oct. 13, 2010, International Society for Advancement of Cytometry Candidate Recommendation (draft), version 1000929, downloaded from http://flowcyt.sf.net/acs/latest.pdf.
International Search Report and Written Opinion dated Jun. 16, 2016 in International application No. PCT/US15/65045.
DeTomaso et al., Aug. 23, 2016, FastProject: a tool for low-dimensional analysis of single-cell RNA-Seq data, BMC Bioinformatics, 17(1):1-12.
Kiselev et al., Aug. 20, 2016, 9. Seurat: analysis of single cell RNA-seq data, https://scrnaseq-course.cog.sanger.ac.uk/website/seurat-chapter.html, retrieved on Jun. 26, 2020, 37 pp.
Melamed et al., May 2, 2007, GenePattern: Multiplot (v2), https://www.genepattern.org/modules/docs/Multiplot/2, retrieved on Jun. 25, 2020, 11 pp.
Amir, El-ad David et al. "viSNE enables visualization of high dimensional single-cell data and reveals phenotypic heterogeneity of leukemia." *Nature biotechnology* 31.6 (2013): 545-552.

(Continued)

*Primary Examiner* — G Steven Vanni
(74) *Attorney, Agent, or Firm* — Knobbe, Martens, Olson & Bear, LLP

(57) ABSTRACT

Some embodiments of the methods provided herein relate to sample analysis and particle characterization methods for large, multi-parameter data sets. Frequency difference gating compares at least two different data sets to identify regions in a multivariate space where a frequency of events from a first data set is different than a frequency of events from the second data set according to a defined threshold.

20 Claims, 6 Drawing Sheets

(56) References Cited

U.S. PATENT DOCUMENTS

| | | |
|---|---|---|
| 2007/0031823 A1 | 2/2007 | Bentwich |
| 2007/0041395 A1 | 2/2007 | Soucek |
| 2007/0128633 A1 | 6/2007 | Zozulya et al. |
| 2007/0219728 A1 | 9/2007 | Papageorgiou et al. |
| 2008/0097917 A1 | 4/2008 | Dicks |
| 2008/0109175 A1 | 5/2008 | Michalak |
| 2008/0154513 A1 | 6/2008 | Kovatchev |
| 2008/0212643 A1 | 9/2008 | McGahhey et al. |
| 2008/0263468 A1 | 10/2008 | Cappione et al. |
| 2009/0070841 A1 | 3/2009 | Buga |
| 2009/0192363 A1 | 7/2009 | Case |
| 2009/0204557 A1 | 8/2009 | Zhang |
| 2009/0246782 A1 | 10/2009 | Kelso et al. |
| 2009/0307757 A1 | 12/2009 | Groten |
| 2010/0042351 A1 | 2/2010 | Covey et al. |
| 2010/0043047 A1 | 2/2010 | Archer |
| 2010/0070459 A1 | 3/2010 | Zigon |
| 2010/0070904 A1 | 3/2010 | Zigon et al. |
| 2010/0161561 A1 | 6/2010 | Moore et al. |
| 2010/0254581 A1 | 10/2010 | Neeser et al. |
| 2011/0066385 A1 | 3/2011 | Rajwa et al. |
| 2011/0099497 A1 | 4/2011 | Fok |
| 2011/0191899 A1 | 8/2011 | Ainley et al. |
| 2011/0282870 A1 | 11/2011 | Herzenberg et al. |
| 2012/0029832 A1 | 2/2012 | Dodgson |
| 2012/0140641 A1 | 6/2012 | Reese et al. |
| 2012/0179779 A1 | 7/2012 | Awasthi |
| 2012/0214190 A1 | 8/2012 | Hou |
| 2012/0215481 A1 | 8/2012 | Covey et al. |
| 2012/0239297 A1 | 9/2012 | Yokota et al. |
| 2012/0245889 A1 | 9/2012 | Zhu et al. |
| 2013/0091135 A1 | 4/2013 | Yokoi et al. |
| 2013/0117298 A1 | 5/2013 | Ray |
| 2013/0177933 A1 | 7/2013 | Malisauskas |
| 2013/0197894 A1 | 8/2013 | Sablinski |
| 2013/0226813 A1 | 8/2013 | Voltz |
| 2013/0289925 A1 | 10/2013 | Jiang et al. |
| 2014/0072189 A1 | 3/2014 | Jena et al. |
| 2014/0154789 A1 | 6/2014 | Polwart et al. |
| 2014/0164564 A1 | 6/2014 | Hoofnagle |
| 2014/0213468 A1 | 7/2014 | Ehrenkranz et al. |
| 2014/0216128 A1 | 8/2014 | Trotter |
| 2014/0222866 A1 | 8/2014 | Joneja |
| 2015/0120883 A1 | 4/2015 | Gurtowski |
| 2015/0295972 A1 | 10/2015 | Hagan |
| 2015/0363563 A1 | 12/2015 | Hallwachs |
| 2016/0122341 A1 | 5/2016 | Vakalopoulos et al. |
| 2016/0130574 A1 | 5/2016 | Sadekova et al. |
| 2016/0170980 A1 | 6/2016 | Stadnisky et al. |
| 2016/0243251 A1 | 8/2016 | Blainey et al. |
| 2016/0328249 A1 | 11/2016 | Simm et al. |
| 2016/0337786 A1 | 11/2016 | Kafle et al. |
| 2016/0362408 A1 | 12/2016 | Vakalopoulos et al. |
| 2016/0370350 A1 | 12/2016 | Rajwa et al. |
| 2017/0102310 A1 | 4/2017 | Xu |
| 2018/0010134 A1 | 1/2018 | Sharp et al. |
| 2018/0165414 A1 | 6/2018 | Almarode et al. |

FOREIGN PATENT DOCUMENTS

| | | |
|---|---|---|
| JP | 05-209821 | 8/1993 |
| JP | 2001-511546 | 8/2001 |
| JP | 2005-352771 | 12/2005 |
| JP | 2006-230333 | 9/2006 |
| JP | 2012-505460 | 3/2012 |
| WO | WO 04/072866 | 8/2004 |
| WO | WO 13/143533 | 10/2013 |
| WO | WO 14/022787 | 2/2014 |

OTHER PUBLICATIONS

Bauer et al. (eds.), Clinical Flow Cytometry: Principles and Applications, Williams & Wilkins (1993).

Hsiao et al. "Mapping cell populations in flow cytometry data for cross-sample comparision using the Friedman-Rafsky test statistic as a distance meaure: FCM Cross-Sample Comparision." Cytometry, Part A, vol. 89, No. 1, pp. 71-88, Aug. 14, 2015.

International Search Report for International Application No. PCT/US2017/065987 dated Feb. 23, 2018.

International Search Report for International Application No. PCT/US2018/034199 dated Jul. 26, 2018.

Jaroszeski et al. (eds.), Flow Cytometry Protocols, Methods in Molecular Biology No. 91, Humana Press (1998).

Macosko, Evan Z et al. "Highly parallel genome-wide expression profiling of individual cells using nanoliter droplets." *Cell* 161.5 (2015): 1202-1214.

Newell et al. Cytometry by Time-of-Fiight Shows Combinatorial Cytokine Expression and Virus-Specific Cell Niches within a Continuum of CD8+ T Cell Phenotypes Immunity, 2012.

Ormerod (ed.), Flow Cytometry: A Practical Approach, Oxford Univ. Press (1994).

Pawley (ed.), Handbook of Biological Confocal Microscopy, 2nd Edition, Plenum Press (1989).

Roederer et al. The genetic architecture of the human immune system: a bioresource for autoimmunity and disease pathogenesis. Cell. Apr. 9, 2015;161(2):387-403. doi: 10.1016/j.cell.2015.02.046. Epub Mar. 12, 2015.

Roederer et al. "Frequency difference gating: A multivariate method for identifying subsets that differ between samples." Cytometry. vol. 45, No. 1, pp. 56-64, Aug. 24, 2001.

Roderer et al. "Probability binning comparison: a metric for quantitating multivariate distribution differences." Cytometry, vol. 45, No. 1, pp. 47-55, Aug. 24, 2001.

Shapiro, Howard. Practical Flow Cytometry, 4th ed., Wley-Liss (2003).

Shekhar, Karthik et al. "Automatic classification of cellular expression by nonlinear stochastic embedding (ACCENSE)." *Proceedings of the National Academy of Sciences* 111.1 (2014): 202-207.

Supplementary European Search Report for Application No. EP 15 86 6701 dated Jun. 21, 2018.

Tirosh, Itay et al. "Dissecting the multicellular ecosystem of metastatic melanoma by single-cell RNA-seq." *Science* 352.6282 (2016): 189-196.

Van den Bulcke, T. et al. SynTReN: A Generator of Synthetic Gene Expression Data for Design and Analysis of Structure Learning Algorithms, BMC Bioinformatics, Jan. 26, 2006; vol. 7, No. 43; pp. 1-12.

Van der Maaten, Laurens, and Geoffrey Hinton. "Visualizing data using t-SNE." *Journal of Machine Learning Research* 9.2579-2605 (2008): 85.

Van Der Maaten, Laurens, Eric Postma, and Jaap Van den Herik. "Dimensionality reduction: a comparative." *J Mach Learn Res* 10 (2009): 66-71.

Roederer, Probability binning comparison: a metric for quantitating univariate distribution differences, Cytometry, 45:37-46, (2001).

\* cited by examiner

{Cell ID 1, Parameter 1 (ID, Value), Parameter 2 (ID, Value), ..., Parameter n (ID, Value)}
{Cell ID 2, Parameter 1 (ID, Value), Parameter 2 (ID, Value), ..., Parameter n (ID, Value)}
......

VISUALIZATION, COMPARATIVE ANALYSIS, AND AUTOMATED DIFFERENCE DETECTION FOR LARGE MULTI-PARAMETER DATA SETS

CROSS-REFERENCE TO RELATED APPLICATION(S)

This application claims the benefit of priority under 35 U.S.C. § 119(e) of U.S. Provisional Patent Application No. 62/511,342, filed May 25, 2017, entitled "APPLIED COMPUTER TECHNOLOGY FOR VISUALIZATION, COMPARATIVE ANALYSIS, AND AUTOMATED DIFFERENCE DETECTION FOR LARGE MULTI-PARAMETER DATA SETS," the entirety of each of which is incorporated herein by reference. Any and all priority claims identified in the Application Data Sheet, or any correction thereto, are also hereby incorporated by reference under 37 C.F.R. § 1.57.

BACKGROUND

Technical Field

This disclosure relates to relates generally to the field of automated particle assessment, and more particularly to computer assisted sample analysis and particle characterization features for large, multi-parameter data sets.

Background

Particle analyzers, such as flow and scanning cytometers, are analytical tools that enable the characterization of particles on the basis of electro-optical measurements such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one or more for each of the distinct dyes to be detected are included in the analyzer. For example, some embodiments include spectral configurations where more than one sensor or detector is used per dye. The data obtained comprise the signals measured for each of the light scatter detectors and the fluorescence emissions.

Particle analyzers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured features. The use of standard file formats, such as an "FCS" file format, for storing data from a particle analyzer facilitates analyzing data using separate programs and/or machines. Using current analysis methods, the data typically are displayed in 1-dimensional histograms or 2-dimensional (2D) plots for ease of visualization, but other methods may be used to visualize multidimensional data.

The parameters measured using, for example, a flow cytometer typically include light at the excitation wavelength scattered by the particle in a narrow angle along a mostly forward direction, referred to as forward scatter (FSC), the excitation light that is scattered by the particle in an orthogonal direction to the excitation laser, referred to as side scatter (SSC), and the light emitted from fluorescent molecules in one or more detectors that measure signal over a range of spectral wavelengths, or by the fluorescent dye that is primarily detected in that specific detector or array of detectors. Different cell types can be identified by their light scatter characteristics and fluorescence emissions resulting from labeling various cell proteins or other constituents with fluorescent dye-labeled antibodies or other fluorescent probes.

Both flow and scanning cytometers are commercially available from, for example, BD Biosciences (San Jose, Calif). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by certain particle analyzers, such as a multi-color flow cytometry, are multidimensional, wherein each cell corresponds to a point in a multidimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; and 6,944,338; and U.S. Pat. Pub. No. 2012/0245889, each incorporated herein by reference.

SUMMARY

The systems, methods, and devices of the disclosure each have several innovative aspects, no single one of which is solely responsible for the desirable attributes disclosed herein.

In one innovated aspect, a computer-implemented method of visualizing differences between n-dimensional data sets is provided. The computer-implemented method may be performed under control of one or more processing devices. The method includes performing frequency difference gating on a first data set of n-dimensional data and a second data set of n-dimensional data. The n-dimensional data includes a plurality of events in a plurality of dimensions. The method further includes generating a visualization from the frequency difference gated data for display via a display device, the visualization showing regions in a multivariate space where a frequency of events from the first data set is different than a frequency of events from the second data set according to a defined threshold.

In some implementations of the computer-implemented method the first and second data sets include multi-parameter cell sample data.

In some implementations, the computer-implemented method also includes adjusting the defined threshold in response to user input and adjusting the visualization based on the adjusted defined threshold. The defined threshold may include or represent a plurality of defined thresholds. The computer-implemented method may include generating the visualization by color coding the regions based at least in part on the frequency difference gating. The defined threshold may include an upper threshold identifying one or more regions classified as having a greater frequency of events from the first data set than the second data set. Additionally or alternatively, the defined threshold may include a lower threshold identifying one or more regions having a greater frequency of events from the second data set than the first data set. In some implementations, computer-implemented method of claim 1, wherein the defined threshold includes mid-range boundaries identifying one or more regions having a similar frequency of events as between the first data set and the second data set.

The method may perform frequency difference gating by generating a multi-dimensional histogram with a plurality of bins per dimension according to a bivariate frequency estimate of each of a plurality of defined distributions within the first data set and the second data set. The frequency difference gating may further include normalizing the histogram by event count. The frequency difference gating may further include generating difference histograms for each element in the normalized histogram. In some implementations, the frequency difference gating further includes a processor bi-normalizing the difference histograms. When using bi-normalized histograms, generating the visualization may include rendering a heat map of the bi-normalized difference histograms.

Some instances of the method include generating a third data set based on at least one gate defined by a user through the visualization. The first data set may include a control sample, such as cell data from health matter or cell data from cancerous matter.

In another innovative aspect, a system is provided. The system includes one or more processing devices and a computer-readable storage medium comprising instructions that, when executed by the one or more processing device, cause the system to receive a threshold for frequency difference gating received data sets, receive a first data set of n-dimensional data including a first plurality of events in a plurality of dimensions, receive a second set of n-dimensional data including a second plurality of events in at least the plurality of dimensions, identify a frequency difference gate defining a population of events based at least in part on frequency difference gating for the first data set of n-dimensional data and the second data set of n-dimensional data, the gate identifying a region in multivariate space where a frequency of events from the first data set is different than a frequency of events from the second data set according to the threshold, and cause display of a visualization including a representation of events from the first data set and the second data set included in the population defined by the frequency difference gate, the visualization showing regions in the multivariate space where the frequency of events from the first data set is different than the frequency of events from the second data set according to the threshold.

In some implementations, the threshold includes at least one of: an upper threshold identifying one or more regions classified as having a greater frequency of events from the first data set than the second data set, a lower threshold identifying one or more regions having a greater frequency of events from the second data set than the first data set, or mid-range boundaries identifying one or more regions having a similar frequency of events as between the first data set and the second data set.

The computer-readable storage medium may include instructions that, when executed by the one or more processing device, cause the system to identify the frequency difference gate by at least generating a multi-dimensional histogram with a plurality of bins per dimension according to a bivariate frequency estimate of each of a plurality of defined distributions within the first data set and the second data set.

DETAILED DESCRIPTION

Figure 1:
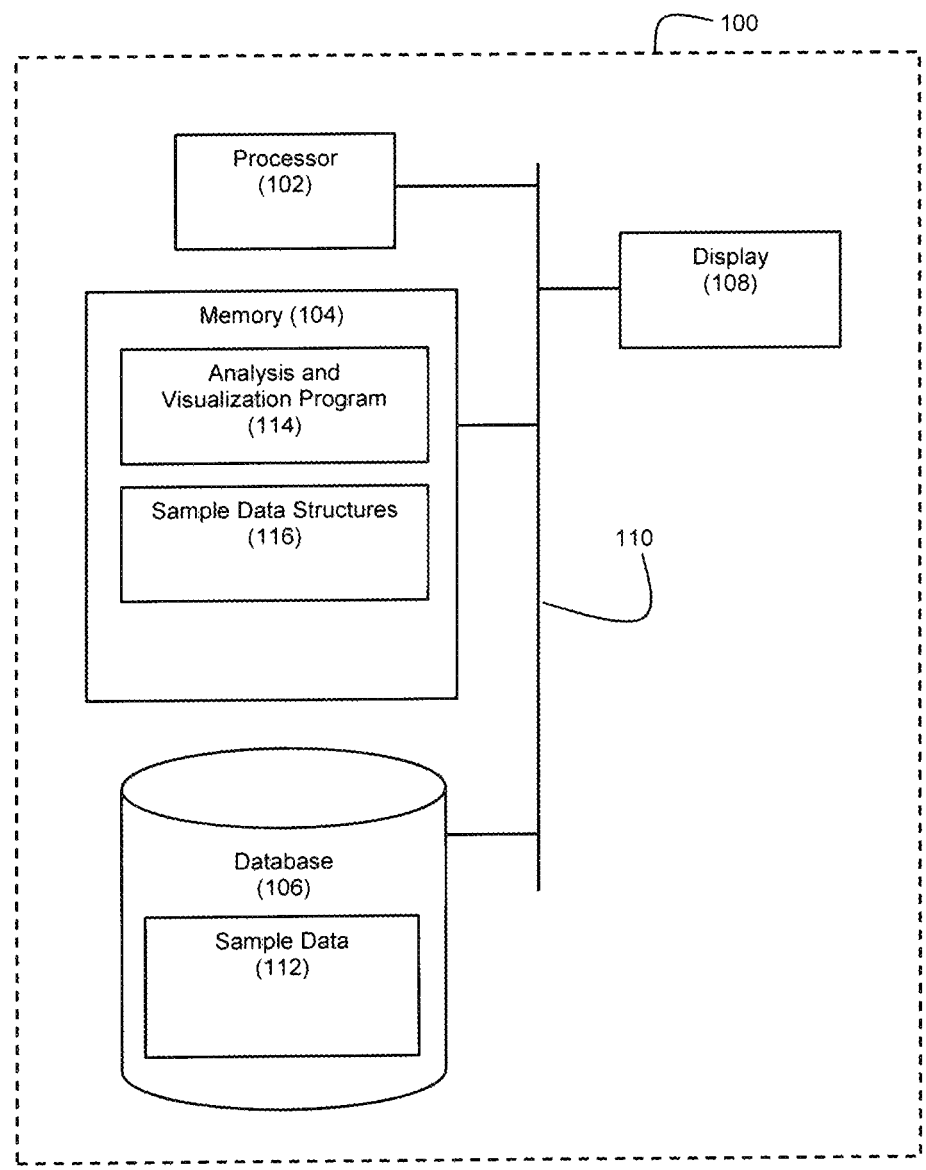
FIG. 1 illustrates an example computer system that can be used to support the innovative data processing and visualization techniques described herein.

A single cell may represent the basic unit of disease, but emerging technologies in flow cytometry (>40 parameters per cell) and single cell sequencing (between 10,000 to more than 60,000 parameters per cell) analysis can be held back by myopic, time-consuming, sequential manual steps or computationally expensive, non-deterministic data reduction approaches. This is a well-documented problem in the art, but the art has struggled to develop solutions to this problem. This lack of determinism prevents meaningful sample comparison, which underpins all types of data analysis but especially life science—comparison to a control or healthy "normal" is a critical component, but single cell science struggles mightily with the best ability to perform these meaningful comparisons in a much-expanded phenotype space.

Features are described to address the problems presented by large multi-parameter data sets, which a human fundamentally cannot explore sufficiently nor perform meaningful comparisons of. Especially when it comes to intra- and inter-sample comparison, humans (e.g., scientific experts) can be incredibly biased based on prior knowledge and expertise. It has been shown that major differences driving biological differences may actually be due to cell subsets that are not included in the manual analysis of data via manual gating (see M. D. Stadnisky, S. Siddiq, J. Almarode, J. Quinn, A. Hart. Reproducible Reduction: Deterministic tSNE using regression trees enables intra-sample comparison. CYTO 2016: XXXI Congress of the International Society for the Advancement of Cytometry. Seattle, Wash. June 2016). That is, phenotypes responsible for a biological response or difference between healthy patients and diseases state may go completely missed by the investigators in a study. Two examples are discussed in more detail below to highlight the limitation of these approaches in comparison of particle data.

To use a specific example, from a study examining how the body counts and regulates immune cell numbers (see Roederer et. al. The genetic architecture of the human immune system: a bioresource for autoimmunity and disease pathogenesis. Cell. 2015 Apr 9;161(2):387-403. doi: 10.1016/j.cell.2015.02.046. Epub 2015 Mar 12.), there are a lot of possible populations ("traits"; "See "Another Application of Technology"") that are known:

Canonical: pre-defined, "known" or described subsets.
$T_{cm}$=CD45RA$^-$ CCR7+CD28+
$T_{REG}$=CD45RO$^+$CD127$^-$CD25$^+$CD39$^+$ For a given panel of antibodies, it is possible that more than 50+canonical populations may be identified. However, and as will be shown in two specific examples below, this approach misses many subsets. In addition, the approach rests on a fundamental assumption that the canonical populations are (1) properly defined and (2) well known. But what if the canonical populations have not been properly defined? Single cell sequencing analysis shows, in an unbiased manner, analytical gaps in using current canonical panels to subset and identify cells. For example, in a recent study performed on innate lymphocyte cells, we defined 3-5 additional markers previously unreported for each canonical ILC subset, and defined 3 "new" child subsets for each canonical subset. In fact, each cell is by definition unique, so one key factor is analyzing what we know from canonical subsets and combining this with the innovative approach describe herein.

An alternative analytical process may include analyzing everything at once, that is, all possible combinations of markers. An advantage of this approach is that the analysis will not overlook any combinations and canonical populations can still be identified. However, a disadvantage of this approach is that, as it necessitates running algorithms which compute over the n-dimensional data set, it is resource intensive. As an example of the quantity of data, we have run these algorithms on data sets which examine 12 proteins and more than 60,000 mRNA and splice variants on every single cell for thousands of cells. This may be deemed a low throughput experiment as compared to other experiments analyzing more than 100,000 parameters per individual cells for many samples which each have hundreds-thousands of cells. Critically, this kind of throughput is held back by an inability to compare between treatments and disease state, thus many studies based on the analytics remain descriptive in nature. As another example, from a study examining how the body counts and regulates immune cell numbers using just one modality (e.g., seven panels examined via flow cytometry), there were:

59 "lineages"
77,941 total subsets
684 MFI Values
Total: 78,683 Traits

. . . and this is before combining with the other data streams available for each twin pair studied.

The resources needed to process such large multi-dimensional data sets may exceed those available or expected to provide a result in an actionable period of time. Resources may include computational resources, power resources, memory resources, network resources, transceiver resources, or the like.

In order to make discovery in n-dimensional space tractable, data reduction can be a useful visualization technique to reduce the number of random variables under consideration and obtain a set "uncorrelated" principal variables. This provides a visual method to explore new parameters which represent a projection of the n-dimensional data which is itself able to be analyzed further. Though there are two approaches for data reduction, feature extraction and feature selection; and feature extraction has been used extensively in single cell science, particularly principal component analysis (PCA) and t-distributed stochastic neighbor embedding (t-SNE).

PCA may be used to extract linearly uncorrelated variables called principal components (e.g., new parameters) which represent the variance in the underlying (e.g., "raw") data. However, we and others have shown that the greatest advantage of PCA is also its downfall—"PCA finds the most optimal representation within the set of possible linear projections of the data is also important limitation—a linear projection may be too restrictive to yield accurate representations." Shekhar, Karthik et al. "Automatic classification of cellular expression by nonlinear stochastic embedding (ACCENSE)." *Proceedings of the National Academy of Sciences* 111.1 (2014): 202-207. In our findings, PCA is unable to identify clusters identified by a scientific expert on a low dimension (e.g., 8-parameter) data set. In addition, in single cell sequencing, PCA is sensitive to transcript number.

To overcome these limitations, there has been much recent work in applying t-SNE to single cell data. t-SNE is a powerful non-linear feature extraction technique. Aspects of t-SNE are described in Van der Maaten, Laurens, and Geoffrey Hinton. "Visualizing data using t-SNE." *Journal of Machine Learning Research* 9.2579-2605 (2008): 85 and Van Der Maaten, Laurens, Eric Postma, and Jaap Van den Herik. "Dimensionality reduction: a comparative." *J Mach Learn Res* 10 (2009): 66-71 each of which are hereby incorporated by reference. t-SNE models each high-dimensional object by a two- or three-dimensional point in such a way that similar objects are modeled by nearby points and dissimilar objects are modeled by distant points. This is useful in biological visualization and analysis, as the nearest neighbors reflect similar cells which may be grouped together into a subset.

t-SNE has been adapted for single cell cytometry in two different approaches using the addition of (1) partitioning and performance as well as clustering (Amir, El-ad David et al. "viSNE enables visualization of high dimensional single-cell data and reveals phenotypic heterogeneity of leukemia." *Nature biotechnology* 31.6 (2013): 545-552.) and (2) clustering and an application (Shekhar, Karthik et al. "Automatic classification of cellular expression by nonlinear stochastic embedding (ACCENSE)." *Proceedings of the National Academy of Sciences* 111.1 (2014): 202-207.) t-SNE has shown promise and has been used successfully to identify populations in single cell sequencing (Macosko, Evan Z et al. "Highly parallel genome-wide expression profiling of individual cells using nanoliter droplets." Cell 161.5 (2015): 1202-1214.; Tirosh, Itay et al. "Dissecting the multicellular ecosystem of metastatic melanoma by single-cell RNA-seq." *Science* 352.6282 (2016): 189-196.)

However, some critical interrelated challenges remain. On challenge is the computational expense. For analytical systems including t-SNE, the computational expense is quantified as slow runtime that scales poorly, $O(N^2)$ for the reference implementation or $O(N \log N)$ for the Barnes-Hut implementation. The computational expense is driven by the number of parameters/traits but also the number of independent particle measurements (e.g., events, cells, etc.). Running over many thousands of parameters and events can lead to a long runtime waiting for analysis, or is simply not feasible without vast resources such as a supercomputer/server cluster.

Another challenge relates to the aforementioned determinism. t-SNE learns a non-parametric mapping of the data, and thus there is no readily available method for out of sample estimation. The result of this is that two runs of t-SNE on the same data set are likely to produce two different visualizations. This non-determinism is inherent to the algorithm, and necessitates the concatenation of data files such as by combining healthy and diseased tissues into one file and then running t-SNE on the combined data file to attempt to visualize differences. This is explained in further detail in Example #2 below.

Another challenge relates to the analytical comparisons that can be performed. Comparison exacerbates both of aforementioned challenges in the extreme—performing a pairwise comparison of N samples leads to $(N(N-1))/2$ comparisons (thus $N^2$ performance), but n-wise comparison is worse than this already poor computational performance. In the face of this challenge, some parameter/trait preselection can occur as not all traits are useful as (1) some are considered "trivial"—cells too infrequent to merit further analysis (<0.5% of a lineage) and (2) some are too variable (either assay or biologically) based on intra-assay and longitudinal variability controls. However, for analytical purposes, one is left with any guidance as to where to focus in the n-dimensional space. Without a means to perform meaningful comparisons, one answer is to focus on obvious differences, which may not accurately reflect the reality and may also be difficult to tease out in an analytically rigorous fashion.

The features described herein, provide a statistically rigorous method to compare complex, high-dimensional data-sets across any subgroups of subjects and brings for the first time, a diagnostic deep phenotyping approach to high-parameter data.

The content of single cell assays has increased substantially in the past several years, but the ability to perform the most fundamental of tasks—comparison— using these high parameter data sets is severely limited. In terms of orders of magnitude, the field has gone from looking at biology with giant binoculars (e.g., 40× magnification) to using the Hubble telescope (e.g., 8,000× magnification), but the field lacks any meaningful way to compare differences between the celestial objects we observe. Systems and methods exist to see and discover but they cannot do much meaningful analytical work.

The features described, example embodiments of which are disclosed herein, overcome limitations in single cell biology. The features unlock n-dimensional data for use as a diagnostic tool. The described approach can be used to stratify patients for precision medicine; reduce manual analysis time; provide a mechanism which rapidly and reproducibly reveals unidentified cell populations; and create the opportunity to compare large single cell studies.

By definition, an immunologist is not a systems-biologist and, as the example using "canonical" populations above shows, this scientist may specialize in studying a handful of available cell types in deep depth when trying to understand disease or immune cell function. This is because becoming an expert in many cell types—their functionality, interactions, and identification—takes time and training.

Consider two real examples which illustrate this bias of known/canonical populations, and show a glaring need for rigorous comparison as an enabler for life science and precision medicine. These examples should be understood to be illustrative of larger problems in life science.

Example 1: CD8+ T Cells in a Vaccine Study

In a high-parameter cytometry study of CD8+ T cells following vaccination, the authors limited their analyses and results to the canonical CD8+ T cell subsets (Newell et. al. Cytometry by Time-of-Flight Shows Combinatorial Cytokine Expression and Virus-Specific Cell Niches within a Continuum of CD8+ T Cell Phenotypes Immunity, 2012.). We analyzed this data further, starting by concatenating (e.g., combining) the CD8+ T cell data together from 6 different patients. We then reduced the 25-parameter data space using t-SNE.

The concatenated CD8+ T-cell data for the 6 different patients are clearly included two different immune signatures. Our experiment found that 4 of the 6 patients were distinguished by cell types which fell outside traditional gates (e.g., "canonical" populations).

This difference in immune signatures illustrates limitations of current analytical approaches. In precision medicine implementations, current frameworks to not provide a rigorous way to compare patients' specific immune signature (e.g., CD8+ T cell response). This suggests that identifying differences between patients can be nearly impossible using current analytical techniques. This in turn, limits the ability to identify the totality of an immune signature, and thus hinders practice of precision medicine.

In discovery implementations, the existing frameworks do not provide a rigorous way to extract all of the cell subsets which may differentiate two completely different responses to the vaccine. The potential for cell types to exist outside the canon illustrates how a focus on canonical populations can drive a published study. This also highlights that there is no tool to simply divide the two patient groups and "ask the data" what is different here?

Example 2: Innate Lymphoid Cells in Cancer and Tissue-Specific Immune Responses

In another example from high-parameter cytometry, we performed a meta-analysis comparing immune responses in healthy tissue and tumor in three different organs—colon, liver, and lungs.

Of note, we have observed the same comparison problem in single cell sequencing of cells, where we would like to rigorously extract the cells which are "plastic" or perhaps are differentiating into another cell subset—represented by the data points of a given color which appear to be part of another cell subset.

For example, consider a t-SNE scatter plot of 847 of the most differentially expressed genes in immune cell subsets (of 60,000 mRNA and splice variants). Color may be used in the scatter plot to represents phenotype using "canonical" definitions via flow cytometry. The 847 genes may include cells whose cluster inclusion is not "predicted" by canonical flow definitions. However, because the scatter plot presents the expressed genes differentiated only by color, it is currently not possible to pull out these cells which are different in any kind of rigorous, automatic manner. These cells may be hidden amongst the canonically analyzed cells leaving potentially significant differences undetected.

Thus, as the above examples illustrate, rather than the curse of dimensionality [R. E. Bellman; Rand Corporation (1957). Dynamic Programming. Princeton University Press. Republished: Richard Ernest Bellman (2003). Dynamic Programming. Courier Dover Publications. & Richard Ernest Bellman (1961). Adaptive Control Processes: a guided tour. Princeton University Press.], the expanded phenotype window, in which each cell subset has biological meaning and could be correlated with disease, but may be missed by the expert, presents a knowledge discordance leading to a deep dive in known phenotypes and little attention paid to other cell subsets. This leads to large amounts of data lying dormant in the discovery process, at all levels in cytometry—e.g. a "standard" 10 color assay=1024 possible phenotypes of interest. In addition, with no way to compare between samples, how is a biologist supposed to focus their attention within the data space e.g. on the phenotypes that really correlate with and thus differentiate/drive disease?

However, collecting more parameters and engaging in this discovery process is not an exercise in "more is more," but rather is critical in finding correlates of morbidity or therapeutic efficacy. Assume that an investigator is looking for a subset of T-cells that is defined by a combination of 4 parameters (a.k.a "markers") which is important in a particular immune response. When using fewer than four markers, the investigator is including other, irrelevant cell populations in our analysis, thereby diluting her ability to detect the cells of interest. As fewer and fewer markers are used, more and more irrelevant are measured cells increasing "noise" and consequently reducing the detection of the important cells i.e. those that correlate with protection. In general, it's harder to find significant associations when making bulk measurements. However, a priori the number of markers necessary to find a correlate of protection is unknown. Protective responses almost certainly comprise cells expressing a pattern of multiple functions. Thus, by examining more markers on more cells, the system can identify cell subsets that may correlate with morbidity or therapeutic efficacy. Using the innovative features described, new and unexpected subsets of import in disease may be identified.

Thus, scientists attempting to leverage single cell technologies in discovery-focused research beyond a narrow area of focus face a difficult, non-deterministic, non-reproducible path.

Some conventional solutions in the art that could be employed to run discovery analysis on this data set exist. One is manual analysis. Manual analysis may include reviewing visualization plots of event data. Another solution may include basic statistics such as K-S, Cox Chi-squared analysis. But this may prove too sensitive. Furthermore, the statistics do not provide a method of gating and typically are limited to univariate analysis.

Another solution may include turning to a bioinformatician. In a rare case, an investigator will collaborate with a bioinformatician who can leverage her specialized skills to analyze the data.

Another approach is to use reduction to help focus the analysis of the multidimensional data. One example of a reduction is tree visualization (SPADE, X-shift, flowSOM) or progression inference (Wanderlust, Pseudotime). However, these reductions are non-deterministic and provide no comparison feature whatsoever. As discussed above, PCA is another reduction option, but comes with validation concerns. t-SNE is another choice, but the issues with this approach are outlined above. For instance, in t-SNE data reduction processing, information from the raw data is lost, but the processing attempts to retain as much "relatedness" as possible. Notwithstanding these efforts, t-SNE may clump data onto 2 dimensions in a way that preserves relatedness in local but not global regions leaving open the chance of overlooking potentially significant differences.

The conventional approaches can be problematic in a number of respects. A need exists in the art for technical improvements with respect to how computer technology can be applied to meaningful identify and visualize salient differences between samples in large multi-parameter data sets. As a solution to this problem, features are described for visualizations based on frequency different gating (FDG).

FIG. 1 illustrates an example computer system 100 that can be used to support the innovative data processing and visualization techniques described herein. The example computer system 100 comprises a processor 102, memory 104, database 106, and display 108 that can be in communication with each other over an interconnect technology such as bus 110.

Processor 102 can take the form of any processor suitable for performing the operations described herein. For example, the CPU of a laptop or workstation would be suitable for use as processor 102. It should be understood that processor 102 may comprise multiple processors, including distributed processors that communicate with each other over a network to carry out tasks described herein (e.g., cloud computing processing resources). Memory 104 can take the form of any computer memory suitable for cooperating with processor 102 in the execution of the tasks described herein. It should be understood that memory 104 may take the form of multiple memory devices, including memory that is distributed across a network. Similarly, database 106 can take the form of any data repository accessible to the processor 102 (e.g., a file system on a computer, relational database, etc.), and it should be understood that database 106 may take the form of multiple distributed databases (e.g., cloud storage). Display 108 can take the form of a computer monitor or screen that is capable of generating the visualizations described herein.

The features described herein are applicable to n-dimensional data sets, which can take the form of sample data 112 (e.g., cellular gene expression data or other particle measurement data). Cellular gene expression data can be generated by next-generation sequencing (e.g. for the measurement of RNA-Sequencing (RNASeq) and single cell RNA sequencing (scRNA-Seq) among other sequencing approaches). However, this is only an example, and other techniques for generating cellular gene expression data may be employed. Additional examples include polymerase chain reaction approaches including digital droplet and reverse transcriptase. Still more examples include RNA measurement by flow cytometry, and microarrays, among others, that produce data files which contain the quantification of DNA and/or RNA, or through software programs that process the raw read data (primary and secondary analysis) to generate the gene expression data files or other biological marker.

The sample data 112 can be characterized as a large multi-parameter data set which poses special technical challenges in terms of difficulty in creating meaningful visualizations, particularly when considered with respect to underlying biology so that biologically-relevant information is meaningful presented to users in a visual manner. For example, the cellular gene expression data may comprise data for large numbers of individual cells and cell populations, with parameters for each cell or cell population that may stretch into 10,000-60,000 or more parameters. Sample data 112 can be read out of files in database 106 and loaded into memory 104 as a plurality of data structures 116 to be manipulated by processor 102 during execution of an analysis and visualization program 114. The analysis and visualization program 114 may comprise processor-executable computer code in the form of a plurality of processor-executable instructions that are resident on a non-transitory computer-readable storage medium such as memory 104.

Figures 2A, 2B:
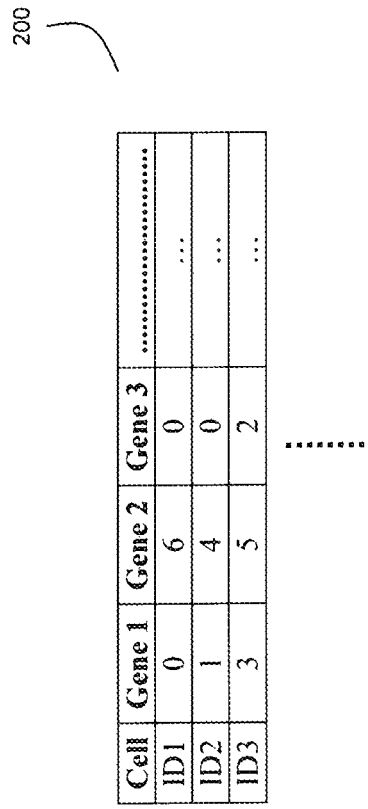
FIG. 2A depicts examples of cellular gene expression data sets.
FIG. 2B depicts a table view of example cellular gene expression data.

FIG. 2A depicts examples of cellular gene expression data sets where each cell (or cell population) is identified by a Cell ID is associated with a plurality of parameters, each parameter having an ID and a value in relation to a Cell ID. As indicated, gene expression data for cells is highly dimensional and the number of parameters for each cell may reach 10,000-60,000 or more parameters, either per cell or per population of cells. Examples of parameters in the cellular data include counts of gene expression in the subject cell for a large number of genes. Thus, Parameter 1 for Cell 1 may correspond to Gene 1 and its value can be a count of expressions for Gene 1 in Cell 1. Similarly, Parameter 2 for Cell 1 may correspond to Gene 2 and its value can be a count of expressions for Gene 2 in Cell 1.

FIG. 2B depicts a table view of example cellular gene expression data. Each row in the table 200 corresponds to a different cell (see the Cell column), and the various columns labeled Gene 1, Gene 2, etc. correspond to different genes and the table cells identify counts of gene expressions for the correspond genes in each subject cell. This table may also include parameters other than genes. For example, the cellular gene expression data 112 may include data values for parameters such as t-distributed stochastic neighbor embedding (tSNE), principal component analysis (PCA), linear discriminant analysis (LDA), etc. in each table cell, where these data values represent an analysis calculation whose value captures differences for individual cells across n parameters. The cellular gene expression data 112 can be stored in any of a number of formats (e.g., as CSV files, database tables (e.g., as relational data in a relational database), spare data representations, binary formats, and others).

Figure 3:
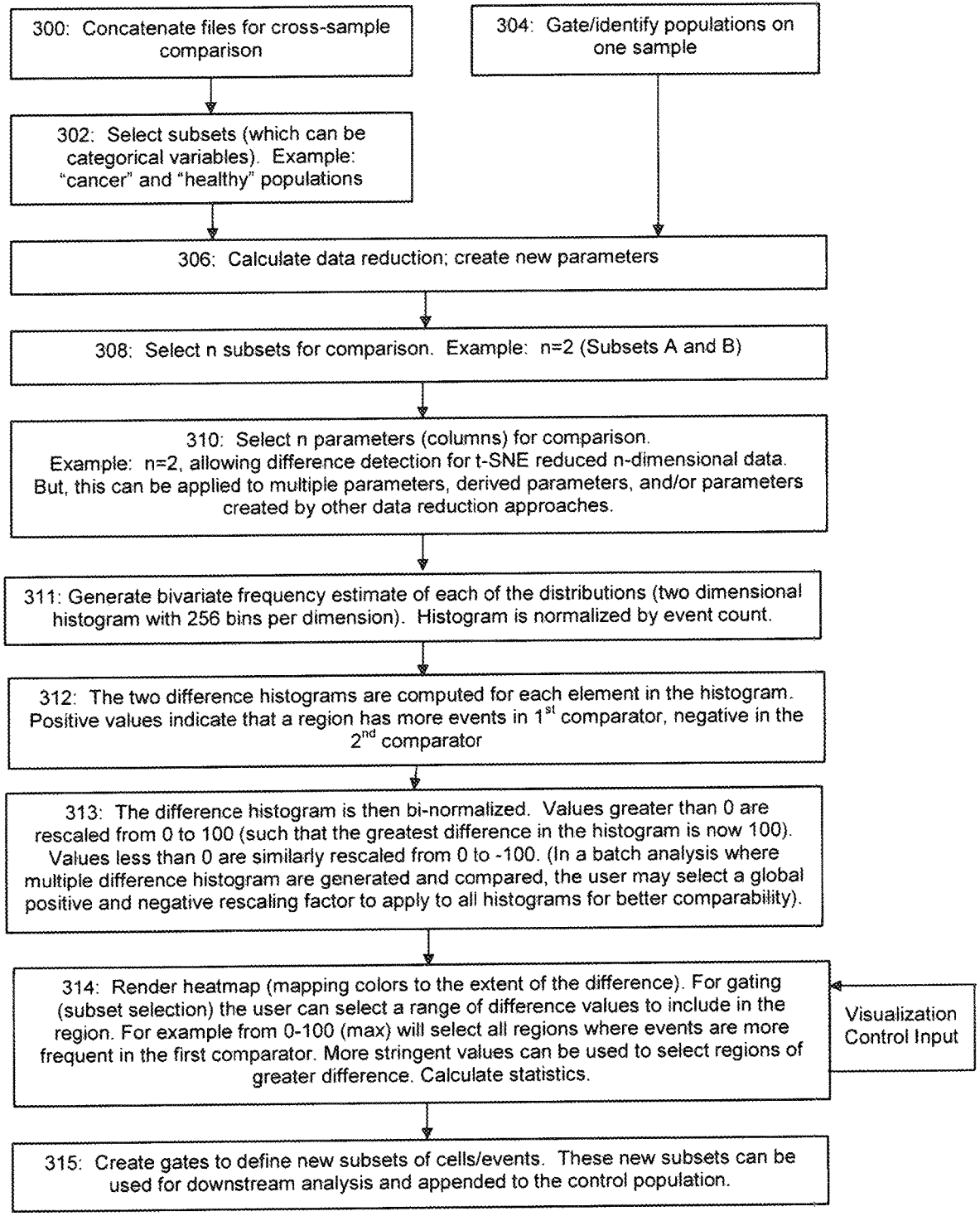
FIG. 3 depicts an example process flow for a method of frequency difference gating and visualization.

FIG. 3 depicts an example process flow for a method of frequency difference gating and visualization. The method may be implemented in whole or in part one or more of the devices described. In some implementations, the analysis and visualization program 114 may include instructions to implement at least part of the method shown. Blocks 300-306 describe options for preparing sample data for analysis.

Under a first option, the system may receive files that are to be concatenated at block 300 for cross-sample comparison. For example, a first file can correspond to a test sample and a second file can correspond to a control sample. Each file corresponds to multi-dimensional sample data, such as the cellular data shown by FIGS. 2A and 2B. Receiving the files may include receiving an uploaded file from a researcher's computer. In some implementations, the files may be received from a particle analyzer such as a flow cytometer. For clarity, the discussion refers to two files, but the concatenation may be based on more than two files.

At block 300, the system concatenates the two files. Concatenating the files may include generating a new parameter in a table or other data structure including the sample data from the files to indicate the source of an entry. For instance, if a table is being used for concatenation, a column that categorically identifies sample data as being either from the first file (test sample) or the second file (control sample) may be populated.

At block 302, the system selects subsets of the concatenated file in response to user input. This could be the drawing of a gate or multiple gates using an interface, or the sub setting of samples and/or their consequent data based on categorical variables e.g. disease state. The values may be received from a user interface and processed by the system to identify the appropriate subsets. For example, when a gate is drawn by a user on a plot presented via a user interface, the events included within the gate may be associated with a subset of the concatenated file.

At block 306, the system performs data reduction operations on two different populations from one file or on a summary file constructed by joining data files for comparison. In both cases, data reduction is performed on one set/matrix of data rather than run separately. An example data reduction operation is t-SNE data reduction. Additional examples of data reduction operations that can be performed include principal component analysis (PCA), linear discriminant analysis (LDA), and local tangent space alignment (LTSA). The data reduction operation yields new parameters for the first and second data sets (e.g., tSNE values for the cells in the table 200). The multi-dimensional data is then ready for comparative analysis starting from block 308 as discussed below. Should the data file already have at least parameters which are the result of data reduction, then block 306 need not be performed.

Under a second option, a user identifies gates or populations within one sample at block 304. This allows a user to comparatively analysis different populations within a single sample (as opposed to cross-sample analysis as with blocks 302-304). Block 306 can then be performed after the gates/populations have been identified, which yields multi-dimensional data ready for comparative analysis starting from block 308.

At block 308, the processor selects n subsets of the n-dimensional data for comparison in response to user input. As an example, n can be 2, thereby defining Subset A and Subset B. These subsets can correspond to first and second data sets that are to be comparatively evaluated via frequency difference gating. For example, the subset selections can be made based on categorical variables such as the parameter that identifies whether sample data is for test populations or control populations (e.g., cancer populations vs. health populations). However, it should be understood that these subsets can be defined based on any parameters in the n-dimensional data (e.g., cancer tissue vs healthy tissue parameter produced by block 300).

Next, at block 310, the processor selects n parameters from Subsets A and B to define the basis for comparing Subsets A and B. As an example, n can be 2. The selected parameters can be parameters present in the n-dimensional data, derived parameters from the n-dimensional data, and/or parameters created by other data reduction approaches. The distributions can come from different samples but also subsets of the same sample which share n parameters for comparison.

Next, at block 311, the processor generates a bivariate frequency estimate which is done by calculating a two dimensional histogram for each comparator sample. The histogram is normalized by event count, and usually but not necessarily smoothed using a variable width kernel smoothing which are the same which are used to generate smoothed contour or pseudocolor plots.

At block 312, the processor calculates two difference histograms for each element (e.g., bin) in the histogram. Positive values indicate that region has more events in first comparator; negative values indicate that the region has more events in the second comparator.

Next, at block 313, the difference histogram is bi-normalized, wherein values greater than 0, corresponding to the region which has more events in the first comparator, are rescaled from 0 to 100 (such that the greatest difference in the histogram is now 100). Values less than 0, corresponding to the region which has more events in the second comparator are similarly rescaled from 0 to −100. It should be understood that in a batch analysis where multiple difference histograms are generated and compared, the user may select a global positive and negative rescaling factor to apply to all histograms for better comparability).

Next, at block 314, the resulting histogram is drawn using a heat map render (mapping colors to the extent of the difference), but it should be understood that this may include rendering using other display types via a display device. At block 314, the processor generates a visualization that visualizes the differences between Subsets A and B according to a bivariate distribution. This is a powerful new visualization that provides users with new insights into multi-parameter data sets that were not available with conventional systems in the art. The visualization provides an overlay of the populations chosen for Subsets A and B. This overlay can be color coded to visually indicate the areas most frequently populated from Subset A relative to Subset B (e.g., Color 1) and the areas most frequently populated from Subset B relative to Subset A (e.g., Color 2).

Figure 4A:
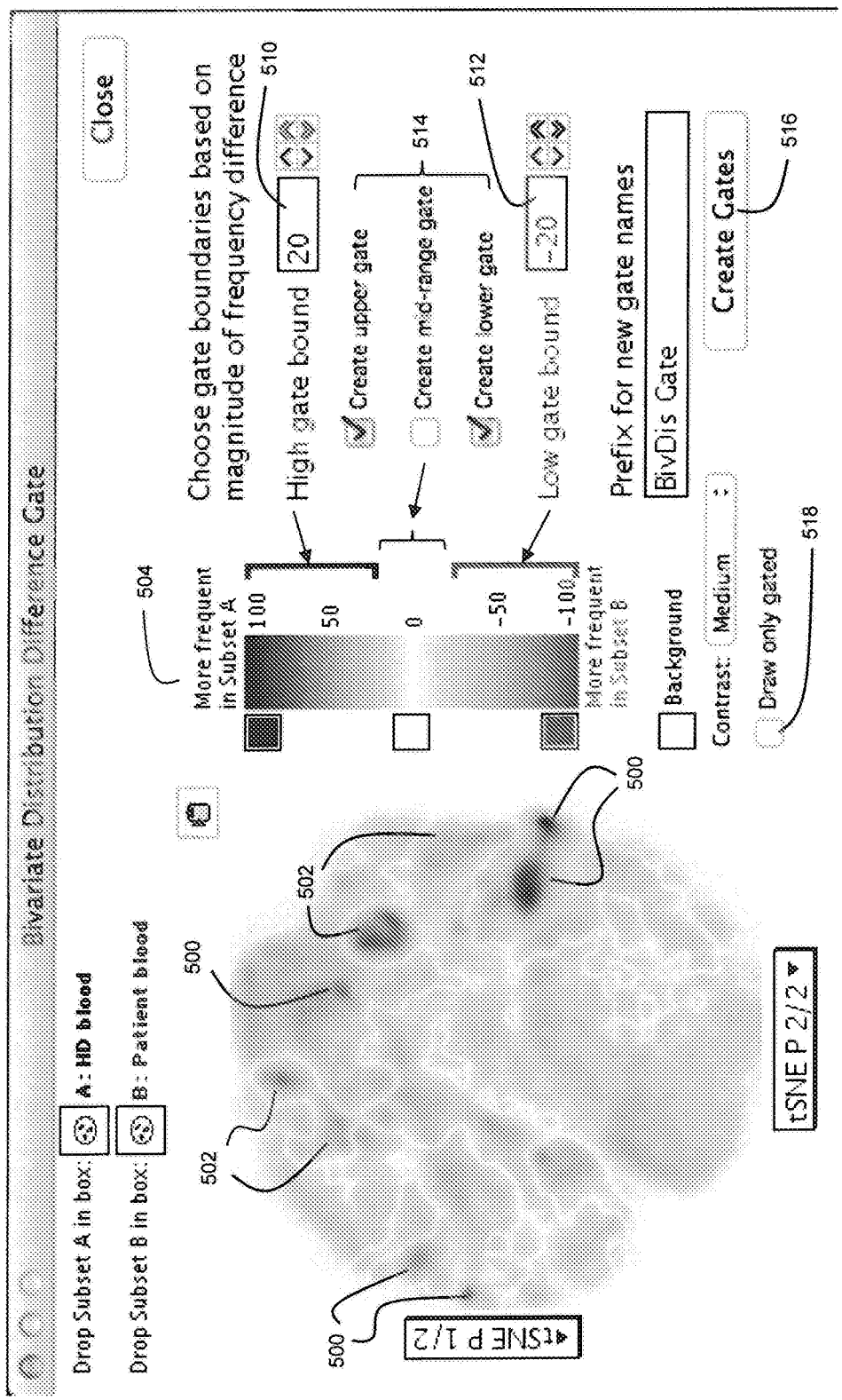
FIGS. 4A-4C show example frequency difference gating visualizations that can be generated.

FIG. 4A shows an example of such a visualization. FIG. 4A shows a plot that overlays two samples (Subset A: HD blood; Subset B: Patient blood) in parameter space (t-SNE P 1/2 vs. t-SNE P 2/2). Regions (e.g., 500 in FIG. 4A) in the plot where frequency difference gating reveals a higher frequency of events in Subset A relative to Subset B according to a defined threshold are shown in a first color/shading (e.g., blue), and regions (e.g., 502 in FIG. 4A) in the plot where frequency difference gating reveals a higher frequency of events in Subset B relative to Subset A according to a defined threshold are shown in a second color/shading (e.g., red). The color coding can modulate the intensity of the coloring/shading as a function of the magnitude of the frequency differences, as indicated by legend 504 of the visualization.

The defined thresholds for the frequency difference gating can be fixed thresholds, or they can be adjustable thresholds. For example, the visualization can be an interactive visualization where a user is able to adjust the defined threshold(s) via inputs 510 and 512. In the example of FIG. 4A, the user can define a threshold for the high gate bound (more frequent in Subset A than Subset B) via input 510. Specifically, for gating (subset selection), the user inputs a range of difference values to include in the region. For example from 0 to 100 (max) will select all regions where events are more frequent in the first comparator. More stringent values can be used to select regions of greater difference. In the example of FIG. 4A, the user can also define a threshold for the low gate bound (more frequent in Subset B than Subset A) via input 512. However, it should also be understood that a single threshold can be used, in which case the gating is a binary choice between "More Frequency in Subset A" or "More Frequency in Subset B", although the inventors believe that multiple thresholds as shown by FIG. 4A can provide deeper insights into the biological properties of the data.

Based on this visualization, the user can choose whether to create any gates based on the presented frequency differences at block 315 of FIG. 3. User input area 514 allows the user to identify which of a plurality of gates can be creates from the data upon selection of the "Create Gates" button 516. The choices in area 514 include (1) a "Create upper gate" option, which gates the regions where events are more frequent in the first comparator (0 to 100), set using field 510, more stringent values can be used to select regions of greater difference, (2) a "Create lower gate" option, which gates the regions events are more frequent in the second comparator (0 to −100), set using 512, more stringent values can be used to select regions of greater difference, and (3) a "Create mid-range gate" option, which gates the regions that fall outside the upper and lower gates. These different gated regions can provide a user with different insights into the data because regions that are different in some manner (e.g., higher or lower event frequency) or the same in some manner may be biologically interesting to the user.

Figure 4B:
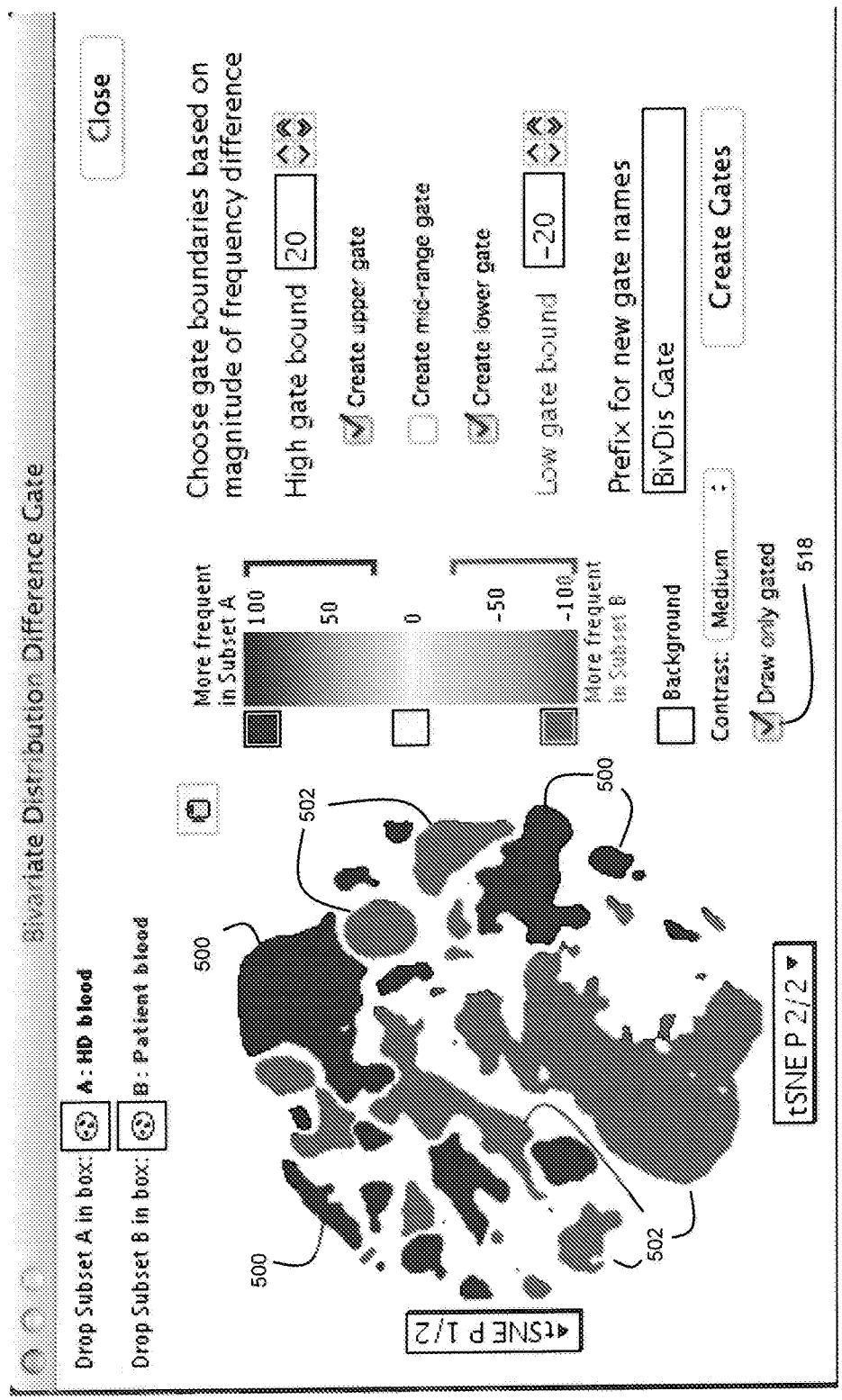

FIG. 4B shows an example of how the visualization can be interactively adjusted based on user input. In FIG. 4B, the user has selected the option for controlling the plot to show only the defined gated regions, which in this case is a defined upper gate where the events are more frequent in the first comparator is equal to 20 (of 100) and the events are more frequent in the second comparator is set to −20 (of −100). This yields color coded/shaded regions (e.g., 500/502) as shown in FIG. 4B.

Figure 4C:
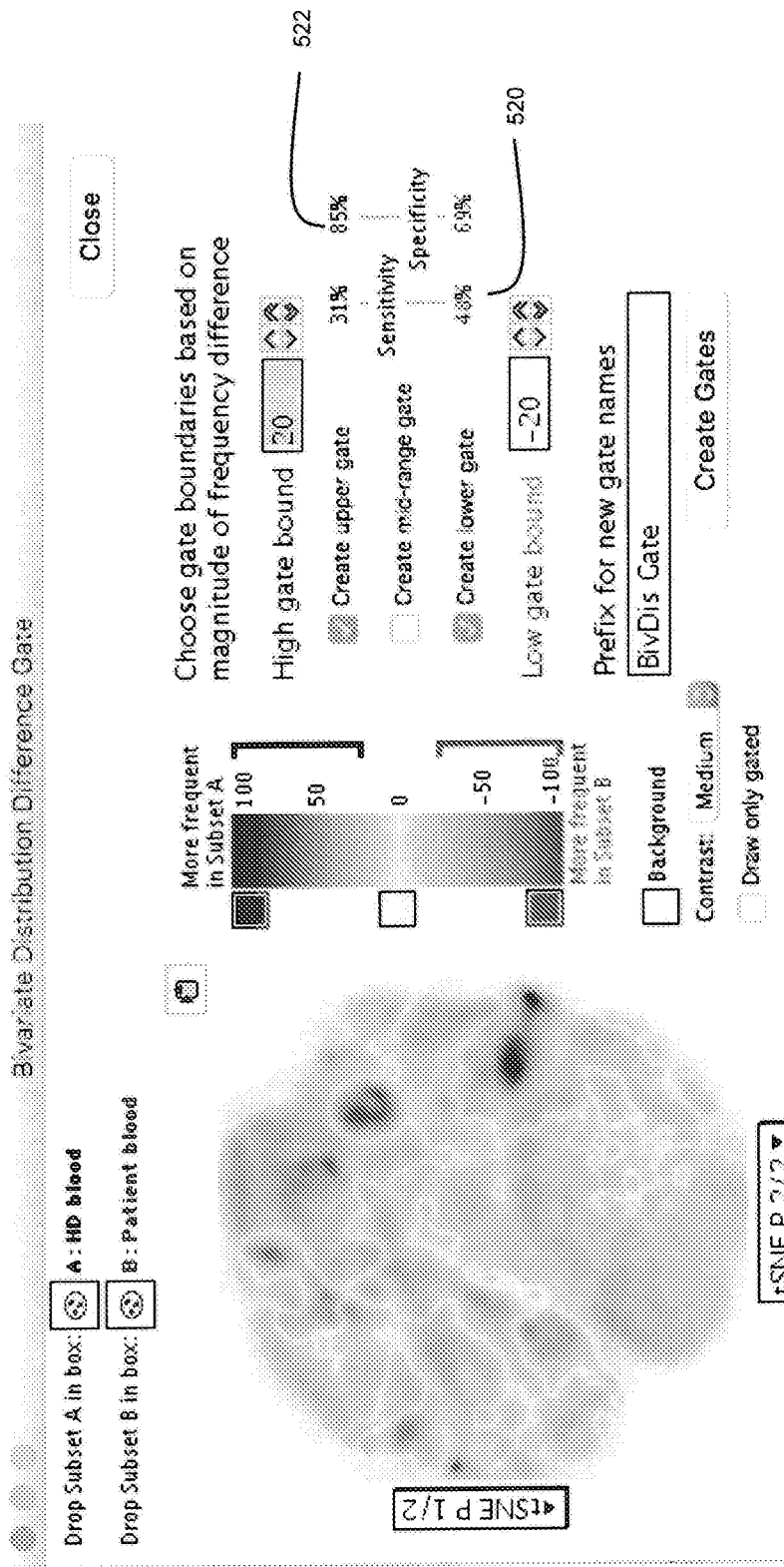

Additional examples of interactive controls over the visualization can include a sensitivity control and a specificity control. The three statistics—specificity, sensitivity, p value—are only calculated if each comparator is comprised of a group of subjects e.g. first comparator is itself made up of subsets from n subjects. Then, the statistics can be calculated as to what fraction of events in each subject fall into the selected region. These are used for sensitivity and specificity calculations. P value is calculated, though not shown, which is student's T-test on the fraction of events in the gate for group 1 subjects vs group 2 subjects. The sensitivity control can govern what fraction of the events in the compared population would appear in the gate when created, shown in FIG. 4C as slider control 520. The specificity control can govern what fraction of the events in the gate come from the compared population—e.g., the "purity" of the gate, shown in FIG. 4C as slider control 521.

Upon selection of gating choices in area 514 and button 516, the system generates a data set corresponding to the defined gates (block 320). These defined gates can then be clustered or subsetted further to explore all of the differences between n samples. In addition, the gates can be explored for their other parameters for the expression of proteins of genes to identify the cell subsets that make up these populations. The subsets of cells/events defined by the created gate can be appended to the control population.

Thus, it should be understood that the frequency difference gating techniques described herein provide users with a powerful tool exploring complex multivariate distributions and quantitating differences between samples based on multiple measurements. Such a tool allows users to generate insights into large multi-parameter sets that are unavailable from conventional systems in the art. For example, frequency different gating provides an unbiased tool for rapidly identifying regions in multivariate space in which the frequency of events is statistically significantly different between samples. These identified regions can be used in any of a number of useful ways, including but not limited to (1) identifying cells that respond to a stimulus, and (2) identifying disease-associated differences in phenotype or representation. Also, frequency difference gating can be applied to other samples to quantitate the number of "responders".

Through these and other features, example embodiments of the invention provide significant technical advances in the applied bioinformatics arts.

As used herein, the terms set forth with particularity below have the following definitions. If not otherwise defined in this section, all terms used herein have the meaning commonly understood by a person skilled in the arts to which this invention belongs.

As used herein, "system," "instrument," "apparatus," and "device" generally encompass both the hardware (e.g., mechanical and electronic) and, in some implementations, associated software (e.g., specialized computer programs for graphics control) components.

As used herein, an "event" generally refers to the packet of data measured from a single particle, such as cells or synthetic particles. Typically, the data measured from a single particle include a number of parameters, including one or more light scattering parameters, and at least one parameter or feature derived from fluorescence detected from the particle such as the intensity of the fluorescence. Thus, each event is represented as a vector of measurements and features, wherein each measured parameter or feature corresponds to one dimension of the data space. In some embodiments, the data measured from a single particle may include image, electric, temporal, or acoustic data. In some biological applications, event data may correspond to quantitative biological data indicating expression of a particular protein or gene.

As used herein, a "population", or "subpopulation" of particles, such as cells or other particles, generally refers to a group of particles that possess properties (for example, optical, impedance, or temporal properties) with respect to one or more measured parameters such that measured parameter data form a cluster in the data space. Thus, populations are recognized as clusters in the data. Conversely, each data cluster generally is interpreted as corresponding to a population of a particular type of cell or particle, although clusters that correspond to noise or background typically also are observed. A cluster may be defined in a subset of the dimensions, e.g., with respect to a subset of the measured parameters, which corresponds to populations that differ in only a subset of the measured parameters or features extracted from the measurements of the cell or particle.

As used herein, a "gate" generally refers to a classifier boundary identifying a subset of data of interest. In cytometry, a gate may bound a group of events of particular interest. As used herein, "gating" generally refers to the process of classifying the data using a defined gate for a given set of data, where the gate may be one or more regions of interest combined, in some instances, using Boolean logic.

As used herein, an "event" generally refers to the assembled packet of data measured from a single particle, such as cells or synthetic particles). Typically, the data measured from a single particle include a number of parameters or features, including one or more light scattering parameters or features, and at least one other parameter or feature derived from measured fluorescence. Thus, each event is represented as a vector of parameter and feature measurements, wherein each measured parameter or feature corresponds to one dimension of the data space.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML, document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed graphics processor, which may include one or more processors, such as one or more digital signal processors (DSPs), configurable microprocessors, an application specific integrated circuits (ASICs), field programmable gate arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a specialized graphic control card.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A computer-implemented method of visualizing differences between n-dimensional data sets, the computer-implemented method comprising:
   under control of one or more processing devices,
      receiving at least one threshold for frequency difference gating received data sets;
      receiving a first data set of n-dimensional data including a first plurality of flow cytometry events, corresponding to a first sample, in a plurality of first dimensions;
      receiving a second data set of n-dimensional data including a second plurality of flow cytometry events, corresponding to a second sample for cross-sample comparison with the first sample, in at least the plurality of first dimensions;
      concatenating the first data set and the second data set to obtain a concatenated data set;
      performing dimensionality reduction on the concatenated data set to obtain a mapping of events of the concatenated data set in a multivariate space defined by second dimensions different from and fewer than the plurality of first dimensions;
      identifying a frequency difference gate defining a population of events based at least in part on frequency difference gating performed on the mapping of events, the gate identifying a region in the multivariate space where a frequency of events from the first data set is different than a frequency of events from the second data set according to the at least one threshold; and
      generating a visualization from the frequency difference gated data for display via a display device, the visualization including a representation of events from the first data set and the second data set included in the population defined by the frequency difference gate, the visualization showing regions in the multivariate space where the frequency of events from the first data set is different than the frequency of events from the second data set according to the at least one threshold.

2. The computer-implemented method of claim 1, wherein the first and second data sets comprise multiparameter cell sample data.

3. The computer-implemented method of claim 1, wherein the at least one threshold includes an upper threshold identifying one or more regions classified as having a greater frequency of events from the first data set than the second data set.

4. The computer-implemented method of claim 1, wherein the at least one threshold includes a lower threshold identifying one or more regions having a greater frequency of events from the second data set than the first data set.

5. The computer-implemented method of claim 1, wherein the at least one threshold includes mid-range boundaries identifying one or more regions having a similar frequency of events as between the first data set and the second data set.

6. The computer-implemented method of claim 1, wherein performing frequency difference gating comprises:
   generating a multi-dimensional histogram with a plurality of bins per dimension according to a bivariate frequency estimate of each of a plurality of defined distributions within the first data set and the second data set.

7. A system comprising:
one or more processing devices; and
a computer-readable storage medium comprising instructions that are configured to, when executed by the one or more processing devices, cause the system to:
   receive at least one threshold for frequency difference gating received data sets;
   receive a first data set of n-dimensional data including a first plurality of flow cytometry events, corresponding to a first sample, in a plurality of first dimensions;
   receive a second data set of n-dimensional data including a second plurality of flow cytometry events, corresponding to a second sample for cross-sample comparison with the first sample, in at least the plurality of first dimensions;
   concatenate the first data set and the second data set to obtain a concatenated data set;

perform dimensionality reduction on the concatenated data set to obtain a mapping of events of the concatenated data set in a multivariate space defined by second dimensions different from and fewer than the plurality of first dimensions;

identify a frequency difference gate defining a population of events based at least in part on frequency difference gating performed on the mapping of events, the gate identifying a region in the multivariate space where a frequency of events from the first data set is different than a frequency of events from the second data set according to the at least one threshold; and display a visualization including a representation of events from the first data set and the second data set included in the population defined by the frequency difference gate, the visualization showing regions in the multivariate space where the frequency of events from the first data set is different than the frequency of events from the second data set according to the at least one threshold.

8. The system of claim 7, wherein the instructions are further configured to cause the system to:

adjust the at least one threshold in response to user input; and adjust the visualization based on the adjusted at least one threshold.

9. The system of claim 7, wherein the at least one threshold comprises a plurality of thresholds.

10. The system of claim 7, wherein displaying the visualization comprises displaying the regions with color coding indicating relative differences in event frequency between the first and second data sets, based at least in part on the frequency difference gate.

11. The system of claim 7, wherein the instructions are further configured to cause the system to:

generate a third data set based on at least one gate defined by a user through the visualization.

12. The system of claim 7, wherein the first sample comprises a control sample.

13. The system of claim 12, wherein the control sample corresponds to healthy matter.

14. The system of claim 12, wherein the control sample corresponds to cancerous matter.

15. The system of claim 7, wherein the at least one threshold includes at least one of:

an upper threshold identifying one or more regions classified as having a greater frequency of events from the first data set than the second data set;

a lower threshold identifying one or more regions having a greater frequency of events from the second data set than the first data set; or two thresholds corresponding to mid-range boundaries identifying one or more regions having a similar frequency of events as between the first data set and the second data set.

16. The system of claim 7, wherein the computer-readable storage medium comprises instructions that are configured to, when executed by the one or more processing device, cause the system to identify the frequency difference gate by at least:

generating a multi-dimensional histogram with a plurality of bins per first dimension according to a bivariate frequency estimate of each of a plurality of defined distributions within the first data set and the second data set.

17. The system of claim 16, wherein identifying the frequency difference gate further comprises:

normalizing the multi-dimensional histogram by event count.

18. The system of claim 17, wherein identifying the frequency difference gate further comprises:

generating difference histograms for each element in the normalized histogram.

19. The system of claim 18, wherein identifying the frequency difference gate further comprises:

bi-normalizing the difference histograms.

20. The system of claim 19 wherein displaying the visualization comprises:

rendering a heat map of the bi-normalized difference histograms.

* * * * *